US008052755B2

(12) United States Patent
Naidu

(10) Patent No.: US 8,052,755 B2
(45) Date of Patent: Nov. 8, 2011

(54) ULNAR HEAD PROSTHESIS SYSTEM

(75) Inventor: Sanjiv Naidu, Lititz, PA (US)

(73) Assignee: Remi Sciences, Inc., Lititz, PA (US)

( * ) Notice: Subject to any disclaimer, the term of this patent is extended or adjusted under 35 U.S.C. 154(b) by 0 days.

(21) Appl. No.: 12/361,657

(22) Filed: Jan. 29, 2009

(65) Prior Publication Data
US 2009/0281632 A1 Nov. 12, 2009

Related U.S. Application Data

(63) Continuation-in-part of application No. 12/118,157, filed on May 9, 2008, now Pat. No. 7,875,082.

(51) Int. Cl.
*A61F 2/42* (2006.01)
(52) U.S. Cl. .................................................. 623/21.12
(58) Field of Classification Search .... 623/20.11–20.16, 623/16.11, 17.14, 22.4, 22.42, 23.15, 20.35, 623/22.15–22.18, 17.11, 20.36–21.19
See application file for complete search history.

(56) References Cited

U.S. PATENT DOCUMENTS

| | | | | | |
|---|---|---|---|---|---|
| 3,466,670 | A | * | 9/1969 | Christiansen | 623/22.43 |
| 3,506,982 | A | * | 4/1970 | Steffee | 623/21.16 |
| 3,593,342 | A | * | 7/1971 | Niebauer et al. | 623/23.41 |
| 3,694,821 | A | | 10/1972 | Moritz | 623/20.22 |
| 3,795,922 | A | * | 3/1974 | Herbert et al. | 623/20.22 |
| 3,837,008 | A | * | 9/1974 | Bahler et al. | 623/21.13 |
| 3,868,730 | A | * | 3/1975 | Kaufer et al. | 623/20.22 |
| 3,909,853 | A | * | 10/1975 | Lennox | 623/21.13 |
| 3,916,451 | A | * | 11/1975 | Buechel et al. | 623/23.4 |
| 3,978,528 | A | * | 9/1976 | Crep | 623/19.12 |
| 4,003,096 | A | * | 1/1977 | Frey | 623/21.13 |
| 4,040,130 | A | * | 8/1977 | Laure | 623/21.13 |
| 4,100,626 | A | | 7/1978 | White | |
| 4,106,128 | A | * | 8/1978 | Greenwald et al. | 623/21.13 |

(Continued)

FOREIGN PATENT DOCUMENTS

DE  4445892  *  6/1996

(Continued)

OTHER PUBLICATIONS

Willis, A. A. et al., "Arthroplasty of the Distal Radioulnar Joint Using a New Ulnar Head Endoprosthesis: Preliminary Report," *The Journal of Hand Surgery*, 32A:2, pp. 177-189, Feb. 2007.

(Continued)

*Primary Examiner* — Alvin J Stewart
(74) *Attorney, Agent, or Firm* — Glenn M. Massina; Fox Rothschild LLP

(57) ABSTRACT

An ulnar prosthesis assembly comprising a head formed with a curved surface extending between opposed ends and a stem. One of the ends of the head has an attachment bore defined therein. The attachment bore generally has a first diameter and includes an attachment groove thereabout with a second diameter greater than the first diameter to define at least one attachment shoulder. The stem has a stem body extending between a proximal end configured for implantation in a target bone and a distal end configured to be received in the attachment bore. The distal end has a locking flange extending radially therefrom. The locking flange defines a locking shoulder having a diameter greater than the first diameter such that upon receipt in the attachment bore, the locking shoulder engages the attachment shoulder.

25 Claims, 15 Drawing Sheets

U.S. PATENT DOCUMENTS

| | | | | |
|---|---|---|---|---|
| 4,180,871 | A * | 1/1980 | Hamas | 623/21.13 |
| 4,259,752 | A * | 4/1981 | Taleisnik | 623/21.13 |
| 4,276,660 | A * | 7/1981 | Laure | 623/21.16 |
| 4,304,011 | A * | 12/1981 | Whelan, III | 623/21.16 |
| 4,307,473 | A * | 12/1981 | Weber | 623/21.12 |
| 4,352,212 | A * | 10/1982 | Greene et al. | 623/21.16 |
| 4,645,505 | A | 2/1987 | Swanson | |
| 4,677,971 | A | 7/1987 | Lindemann | |
| 4,784,661 | A | 11/1988 | Beckenbaugh et al. | |
| 4,936,854 | A | 6/1990 | Swanson | |
| 4,944,758 | A * | 7/1990 | Bekki et al. | 623/21.15 |
| 4,955,915 | A | 9/1990 | Swanson | |
| 4,963,155 | A * | 10/1990 | Lazzeri et al. | 623/22.42 |
| 4,964,869 | A * | 10/1990 | Auclair et al. | 623/22.43 |
| 5,002,578 | A * | 3/1991 | Luman | 623/22.42 |
| 5,037,440 | A * | 8/1991 | Koenig | 623/21.19 |
| 5,080,685 | A * | 1/1992 | Bolesky et al. | 623/22.42 |
| 5,133,761 | A * | 7/1992 | Krouskop | 623/21.16 |
| 5,133,762 | A * | 7/1992 | Branemark | 623/21.12 |
| 5,152,796 | A * | 10/1992 | Slamin | 623/20.15 |
| 5,201,882 | A * | 4/1993 | Paxson | 623/22.42 |
| 5,290,313 | A * | 3/1994 | Heldreth | 623/20.15 |
| 5,413,610 | A * | 5/1995 | Amino et al. | 623/22.43 |
| 5,458,646 | A * | 10/1995 | Giachino et al. | 623/21.12 |
| 5,507,821 | A * | 4/1996 | Sennwald et al. | 623/21.13 |
| 5,628,740 | A * | 5/1997 | Mullane | 606/307 |
| 5,702,470 | A * | 12/1997 | Menon | 623/21.12 |
| 5,782,926 | A * | 7/1998 | Lamprecht | 623/21.11 |
| 5,888,207 | A * | 3/1999 | Nieder et al. | 623/23.15 |
| 5,888,211 | A * | 3/1999 | Sanders | 623/22.4 |
| 5,906,210 | A | 5/1999 | Herbert | |
| 5,906,644 | A * | 5/1999 | Powell | 623/20.15 |
| 5,931,839 | A | 8/1999 | Medoff | |
| 5,951,604 | A * | 9/1999 | Scheker | 623/21.11 |
| 6,048,365 | A * | 4/2000 | Burrows et al. | 623/23.15 |
| 6,059,832 | A | 5/2000 | Menon | |
| 6,132,467 | A * | 10/2000 | Keller | 623/18.11 |
| 6,146,424 | A * | 11/2000 | Gray et al. | 623/20.34 |
| 6,152,961 | A * | 11/2000 | Ostiguy et al. | 623/22.28 |
| 6,168,630 | B1 * | 1/2001 | Keller et al. | 623/21.11 |
| 6,187,049 | B1 * | 2/2001 | Fujikawa et al. | 623/22.4 |
| 6,238,436 | B1 * | 5/2001 | Lob et al. | 623/22.42 |
| 6,302,915 | B1 * | 10/2001 | Cooney et al. | 623/21.12 |
| 6,306,171 | B1 * | 10/2001 | Conzemius | 623/20.11 |
| 6,306,172 | B1 * | 10/2001 | O'Neil et al. | 623/20.15 |
| 6,436,145 | B1 * | 8/2002 | Miller | 623/20.34 |
| 6,440,171 | B1 * | 8/2002 | Doubler et al. | 623/22.42 |
| 6,454,808 | B1 * | 9/2002 | Masada | 623/21.15 |
| 6,613,092 | B1 * | 9/2003 | Kana et al. | 623/20.15 |
| 6,656,225 | B2 * | 12/2003 | Martin | 623/20.12 |
| 6,682,565 | B1 * | 1/2004 | Krishnan | 623/21.16 |
| 6,689,169 | B2 * | 2/2004 | Harris | 623/21.16 |
| 6,709,459 | B1 | 3/2004 | Cooney, III et al. | |
| 6,736,852 | B2 * | 5/2004 | Callaway et al. | 623/19.14 |
| 6,746,486 | B1 | 6/2004 | Shultz et al. | |
| 6,811,568 | B2 * | 11/2004 | Minamikawa | 623/21.15 |
| 6,814,757 | B2 * | 11/2004 | Kopylov et al. | 623/21.11 |
| 6,818,019 | B2 * | 11/2004 | Horber | 623/18.11 |
| 6,824,567 | B2 * | 11/2004 | Tornier et al. | 623/21.18 |
| 6,827,741 | B2 | 12/2004 | Reeder | |
| 6,860,903 | B2 * | 3/2005 | Mears et al. | 623/22.11 |
| 6,869,447 | B2 * | 3/2005 | Lee et al. | 623/20.15 |
| 6,890,358 | B2 | 5/2005 | Ball et al. | |
| 6,926,739 | B1 * | 8/2005 | O'Connor et al. | 623/21.18 |
| 6,969,407 | B2 | 11/2005 | Klotz et al. | |
| 6,986,790 | B2 * | 1/2006 | Ball et al. | 623/19.11 |
| 7,001,672 | B2 | 2/2006 | Justin et al. | |
| 7,011,686 | B2 * | 3/2006 | Ball et al. | 623/19.14 |
| 7,044,975 | B2 * | 5/2006 | Cheal et al. | 623/22.42 |
| 7,108,719 | B2 * | 9/2006 | Horber | 623/19.11 |
| 7,108,720 | B2 * | 9/2006 | Hanes | 623/22.21 |
| 7,128,763 | B1 * | 10/2006 | Blatt | 623/18.11 |
| 7,160,329 | B2 * | 1/2007 | Cooney et al. | 623/20.11 |
| 7,160,331 | B2 | 1/2007 | Cooney, III et al. | |
| 7,179,297 | B2 * | 2/2007 | McLean | 623/22.11 |
| 7,241,732 | B2 | 7/2007 | Puzas | |
| 7,470,287 | B2 * | 12/2008 | Tornier et al. | 623/19.13 |
| 7,485,147 | B2 * | 2/2009 | Pappas et al. | 623/21.18 |
| 7,520,902 | B2 * | 4/2009 | Deloge et al. | 623/22.15 |
| 7,531,003 | B2 * | 5/2009 | Reindel | 623/21.12 |
| 7,563,287 | B2 * | 7/2009 | Guerard et al. | 623/21.13 |
| 7,585,329 | B2 * | 9/2009 | McCleary et al. | 623/23.15 |
| 7,608,110 | B2 * | 10/2009 | O'Driscoll et al. | 623/20.11 |
| 7,608,111 | B2 * | 10/2009 | Palmer et al. | 623/21.14 |
| 7,625,408 | B2 * | 12/2009 | Gupta et al. | 623/21.11 |
| 7,708,781 | B2 * | 5/2010 | Scheker | 623/20.11 |
| 7,722,676 | B2 * | 5/2010 | Hanson et al. | 623/21.12 |
| 7,766,970 | B2 * | 8/2010 | Shultz et al. | 623/21.14 |
| 7,875,082 | B2 * | 1/2011 | Naidu | 623/21.12 |
| 2001/0025199 | A1 * | 9/2001 | Rauscher | 623/21.13 |
| 2001/0051831 | A1 * | 12/2001 | Subba Rao et al. | 623/22.42 |
| 2002/0016634 | A1 * | 2/2002 | Maroney et al. | 623/19.14 |
| 2002/0099447 | A1 * | 7/2002 | Mears et al. | 623/22.4 |
| 2003/0023315 | A1 * | 1/2003 | Tornier et al. | 623/21.18 |
| 2003/0074083 | A1 * | 4/2003 | LeGros et al. | 623/23.35 |
| 2003/0135280 | A1 * | 7/2003 | Kopylov et al. | 623/21.12 |
| 2003/0204262 | A1 * | 10/2003 | Ferguson et al. | 623/20.15 |
| 2003/0216813 | A1 | 11/2003 | Ball et al. | |
| 2004/0117025 | A1 | 6/2004 | Reindel | |
| 2004/0138756 | A1 * | 7/2004 | Reeder | 623/21.11 |
| 2004/0171924 | A1 | 9/2004 | Mire et al. | |
| 2004/0220674 | A1 * | 11/2004 | Pria | 623/19.12 |
| 2004/0220678 | A1 * | 11/2004 | Chow et al. | 623/21.11 |
| 2004/0230312 | A1 * | 11/2004 | Hanson et al. | 623/21.12 |
| 2005/0004675 | A1 * | 1/2005 | Shultz et al. | 623/21.14 |
| 2005/0085921 | A1 | 4/2005 | Gupta et al. | |
| 2005/0112168 | A1 | 5/2005 | Puzas | |
| 2005/0123672 | A1 | 6/2005 | Justin et al. | |
| 2005/0137709 | A1 * | 6/2005 | Klotz et al. | 623/21.12 |
| 2005/0171613 | A1 * | 8/2005 | Sartorius et al. | 623/21.13 |
| 2005/0216090 | A1 * | 9/2005 | O'Driscoll et al. | 623/20.32 |
| 2005/0246020 | A1 | 11/2005 | Southworth | |
| 2006/0004431 | A1 | 1/2006 | Fuller et al. | |
| 2006/0004462 | A1 * | 1/2006 | Gupta | 623/21.13 |
| 2006/0030946 | A1 * | 2/2006 | Ball et al. | 623/21.13 |
| 2006/0036330 | A1 | 2/2006 | Shultz et al. | |
| 2006/0052725 | A1 * | 3/2006 | Santilli | 600/587 |
| 2006/0052878 | A1 * | 3/2006 | Schmieding | 623/23.4 |
| 2006/0073356 | A1 | 4/2006 | Justin et al. | |
| 2006/0094645 | A1 | 5/2006 | Lawless | |
| 2006/0116773 | A1 | 6/2006 | Cooney, III et al. | |
| 2006/0161260 | A1 * | 7/2006 | Thomas et al. | 623/21.12 |
| 2006/0167559 | A1 * | 7/2006 | Johnstone et al. | 623/23.41 |
| 2006/0229730 | A1 * | 10/2006 | Railey et al. | 623/21.18 |
| 2006/0229732 | A1 * | 10/2006 | Bachelier | 623/22.42 |
| 2007/0055381 | A1 | 3/2007 | Berelsman et al. | |
| 2007/0112431 | A1 * | 5/2007 | Kofoed | 623/21.18 |
| 2007/0142919 | A1 | 6/2007 | Cooney, III et al. | |
| 2007/0198095 | A1 | 8/2007 | VanDer Meulen et al. | |
| 2007/0202351 | A1 | 8/2007 | Justin et al. | |
| 2007/0213645 | A1 | 9/2007 | Zumeris et al. | |
| 2007/0225820 | A1 * | 9/2007 | Thomas et al. | 623/21.12 |
| 2007/0233134 | A1 | 10/2007 | Bastian et al. | |
| 2007/0287027 | A1 | 12/2007 | Justin et al. | |
| 2008/0051909 | A1 * | 2/2008 | Wolfe et al. | 623/21.12 |
| 2008/0125867 | A1 * | 5/2008 | McCleary et al. | 623/22.4 |
| 2008/0133023 | A1 * | 6/2008 | Schlotterback et al. | 623/22.42 |
| 2008/0133024 | A1 * | 6/2008 | Meswania | 623/22.42 |
| 2008/0195217 | A1 * | 8/2008 | Scheker | 623/20.11 |
| 2008/0249630 | A1 * | 10/2008 | Brunneke | 623/19.12 |
| 2008/0249631 | A1 * | 10/2008 | Hassler et al. | 623/21.11 |
| 2008/0288079 | A1 * | 11/2008 | Leibel | 623/20.11 |
| 2009/0143865 | A1 * | 6/2009 | Hassler et al. | 623/19.11 |
| 2009/0254189 | A1 * | 10/2009 | Scheker | 623/21.11 |
| 2009/0281631 | A1 * | 11/2009 | Naidu | 623/20.11 |
| 2009/0281632 | A1 * | 11/2009 | Naidu | 623/20.11 |
| 2009/0312839 | A1 * | 12/2009 | Scheker et al. | 623/20.11 |
| 2009/0312840 | A1 * | 12/2009 | Morrey | 623/20.11 |
| 2009/0319050 | A1 * | 12/2009 | Palmer et al. | 623/21.12 |
| 2010/0010636 | A1 * | 1/2010 | Shultz et al. | 623/21.12 |
| 2010/0030339 | A1 * | 2/2010 | Berelsman et al. | 623/20.11 |
| 2010/0076568 | A1 * | 3/2010 | Gupta et al. | 623/21.12 |

FOREIGN PATENT DOCUMENTS

| FR | 2680968 | * | 3/1993 |
|---|---|---|---|
| FR | 2770770 A1 | * | 5/1999 |
| JP | 05168656 A | * | 7/1993 |
| WO | WO2006/048520 | * | 5/2006 |

OTHER PUBLICATIONS

Sauerbier, M. et al., "Analysis of Dynamic Distal Radioulnar Convergence After Ulnar Head Resection and Endoprosthesis Implantation," *The Journal of Hand Surgery*, 27A:3, pp. 425-434, May 2002.

Masaoka, S. et al., "Biomechanical Analysis of Two Ulnar Head Prostheses," *The Journal of Hand Surgery*, 27A:5, pp. 845-853, Sep. 2002.

Tay, S. C. et al., "In Vivo Three-Dimensional Displacement of the Distal Radioulnar Joint During Resisted Forearm Rotation," *The Journal of Hand Surgery*, 32A:4, pp. 450-458, Apr. 2007.

Dumontier, C. "History of Ulnar Head Replacement," *Techniques in Hand and Upper Extremity Surgery*, 11:1, pp. 109-114, 2007, Paris, France.

Ascension Orthopedics, "Ascension First Choice DRUJ System Surgical Technique," pp. 1-14, 2006.

* cited by examiner

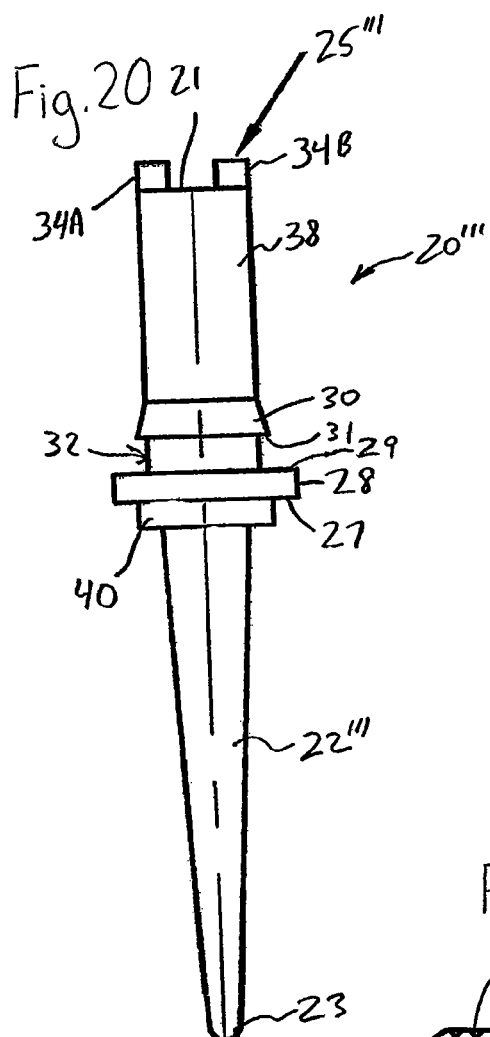
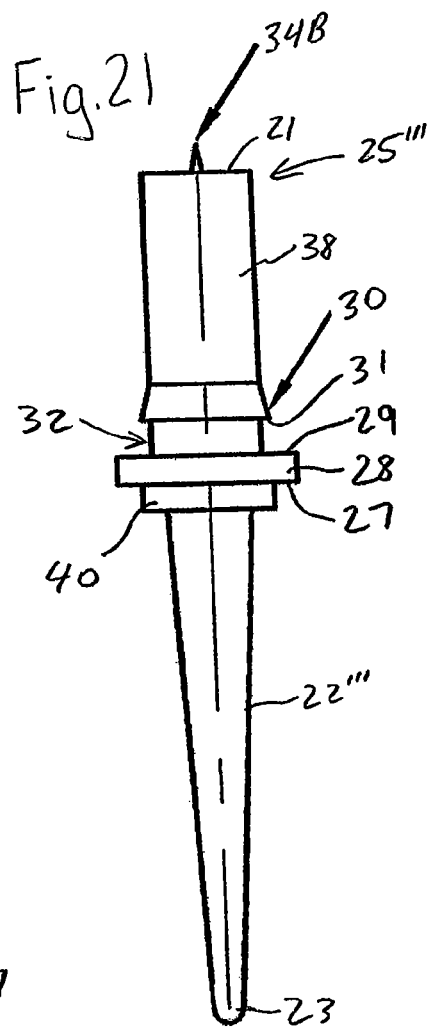
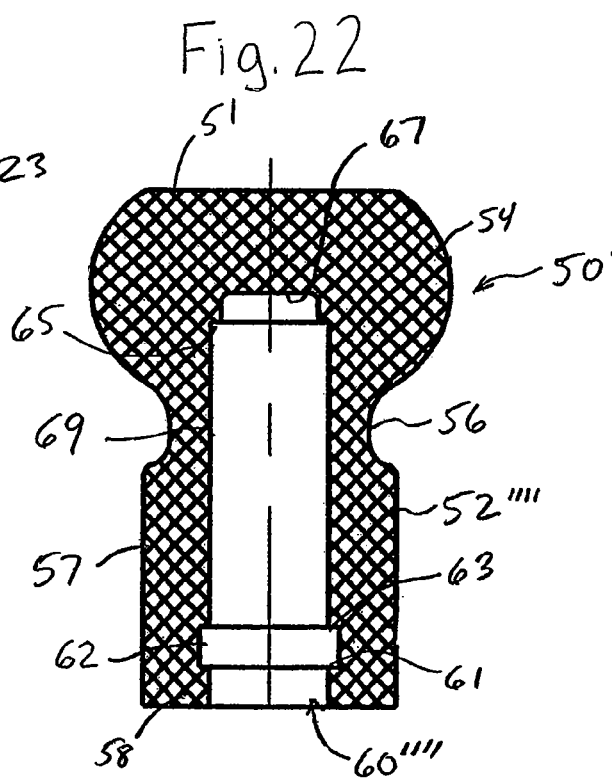

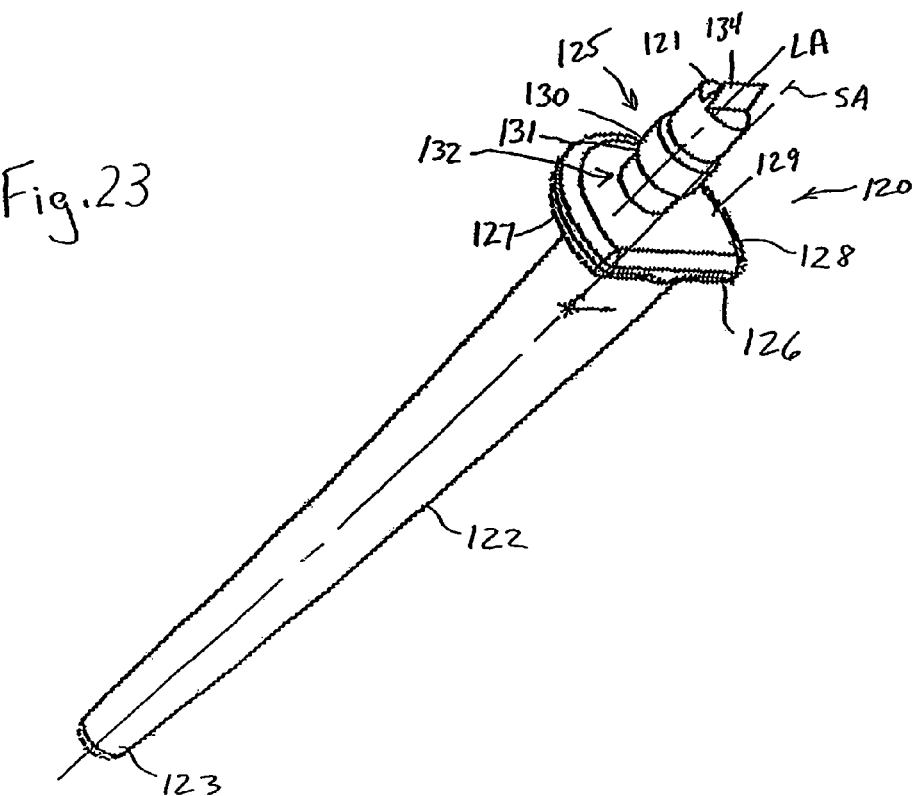
Fig. 23
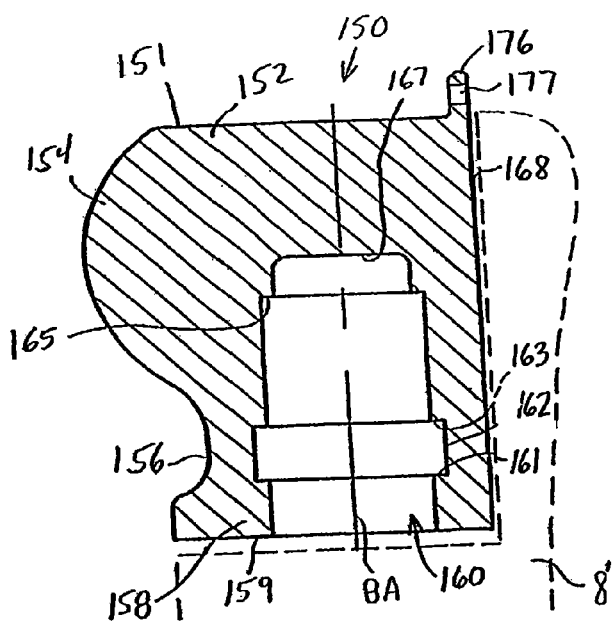
Fig. 24
Fig. 25

ULNAR HEAD PROSTHESIS SYSTEM

BACKGROUND OF THE INVENTION

The present invention relates generally to a prosthesis for the distal radio-ulnar joint and more particularly to a prosthesis for the restoration of pain free rotation of the forearm and stability of the ulna and wrist.

The ulnar head is an integral portion of the distal radio-ulnar joint (DRUJ). The DRUJ is essential for stable forearm rotation and the ulnar head serves as the fixed fulcrum at which the radius sigmoid notch articulates. The radius of curvature of the sigmoid notch is approximately twice that of the ulnar head and the motion between the two surfaces can be accurately described as rolling and sliding.

Disorders of the distal radio-ulnar joint are common and usually associated with pain, weakness, instability and loss of forearm rotation. Any loss of congruity between the sigmoid fossa of the radius and the ulnar head will result in painful loss of forearm rotation. Causes include congenital abnormalities such as Madelung's deformity, radial fractures, inflammatory arthritis and tears of the triangular fibro-cartilage complex. Furthermore, trauma may result in acute dislocation of the distal radio-ulnar joint itself, often in association with radial head fracture and tear of the interosseous membrane. Finally, many patients suffer from painful instability following previous surgical procedures on the distal radio-ulnar joint.

It is important to restore the ulnar head if an individual is to achieve stable and pain free forearm rotation in cases of DJD, inflammatory arthritis, or post traumatic arthritis of the ulnar head. The current salvage procedures without a prosthetic implant include, Darrach resection, hemi-resection, and suave-kapandji; however, all the surgical techniques render the distal ulna unstable leading to recurrence of pain, instability, and weakness.

Although any of the above procedures may produce reasonable results if correctly carried out and in appropriate patients, there are, however, many patients who are discontented with the results of surgery and who are seeking a suitable revision procedure to restore stability and pain free rotation at the distal radio-ulnar joint.

SUMMARY OF THE INVENTION

In at least one embodiment, the present invention provides an ulnar prosthesis assembly comprising a head formed with a curved surface extending between opposed ends and a stem. One of the ends of the head has an attachment bore defined therein. The attachment bore generally has a first diameter and includes an attachment groove thereabout with a second diameter greater than the first diameter to define at least one attachment shoulder. The stem has a stem body extending between a proximal end configured for implantation in a target bone and a distal end configured to be received in the attachment bore. The distal end has a locking flange extending radially therefrom. The locking flange defines a locking shoulder having a diameter greater than the first diameter such that upon receipt in the attachment bore, the locking shoulder engages the attachment shoulder.

In at least one embodiment, the present invention provides an ulnar prosthesis assembly comprising a head formed with a curved surface extending between opposed ends and a stem. One of the ends of the head has an attachment bore defined therein. The attachment bore generally defines a bore end surface. The stem has a stem body extending between a proximal end configured for implantation in a target bone and a distal end configured to be received in the attachment bore. The distal end has a distal end surface with at least one projection extending therefrom and configured such that when the distal end is received in the attachment bore, the at least one projection penetrates the bore end surface and prevents relative rotation between the head and the stem.

In at least one embodiment, the present invention provides an ulnar prosthesis assembly comprising a head formed with a curved surface extending between opposed ends and a stem. One of the ends of the head has an ulnar styloid prominence or process with one or more holes for reattachment of stabilizing soft tissues, the other end having an attachment bore defined therein. The stem has a stem body extending between a proximal end configured for implantation in a target bone and a distal end configured to be received in the attachment bore.

In at least one embodiment, the present invention provides an ulnar prosthesis assembly comprising a head and a stem. The head includes a radially curved surface extending between opposed ends with the curved surface extending circumferentially less than 360° between opposed side edges with an ulnarly flat surface defined between the side edges. The stem has a radial collar extending therefrom between distal and proximal ends thereof, the radial collar configured to complement the curved and flat configuration of the head. The proximal end of the stem is configured for implantation in a target bone and has a first central axis and the distal end of the stem is configured to be received in the attachment bore and has a second central axis that is offset relative to the first central axis.

BRIEF DESCRIPTION OF THE DRAWINGS

FIG. 20 is a front elevation view of a stem in accordance with another alternative embodiment of the present invention.

FIG. 21 is a side elevation view of the stem of FIG. 20.

FIG. 22 is a cross-sectional view of an exemplary head for use with the stem of FIGS. 20 and 21.

FIG. 23 is an isometric view of a stem in accordance with an alternative embodiment of the present invention.

FIG. 24 is a top plan view of an exemplary head for use with the stem of FIG. 23.

FIG. 25 is a cross-sectional view along the lines 25-25 in FIG. 24.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

Referring to FIGS. 1-8, a prosthesis assembly 10 in accordance with an embodiment of the present invention will be described. The prosthesis assembly 10 is a modular assembly generally comprising a stem 20 and a head 50. The stem 20 is configured to be implanted in the intermedullary canal of an ulnar bone. In the present embodiment, the prosthesis assembly 10 is configured to provide for a total ulnar head replacement, however, the present invention may also be used for partial or hemi ulnar head replacement as described below.

Figure 1:
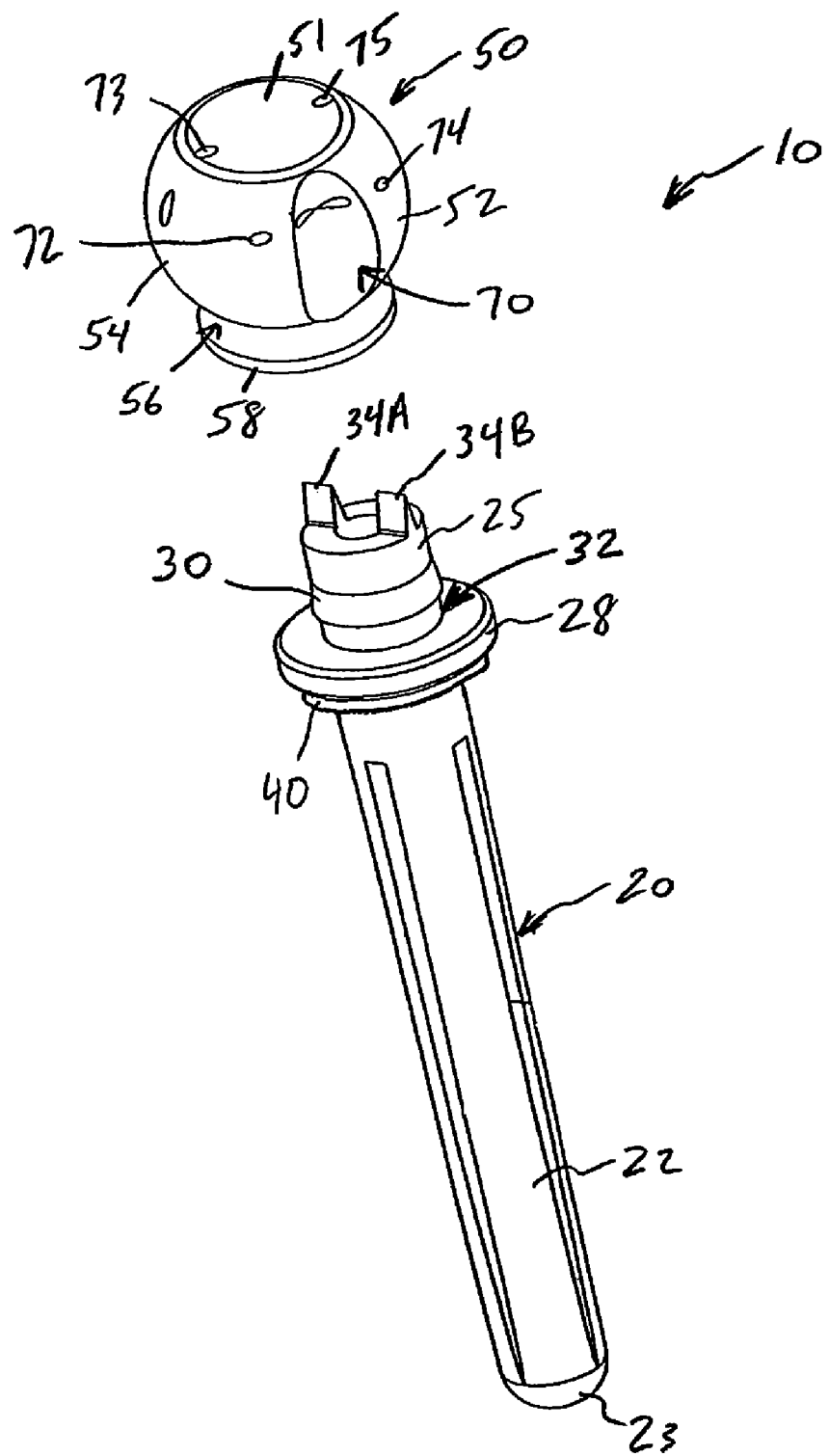
FIG. 1 is an exploded, isometric view of a prosthesis assembly in accordance with an embodiment of the present invention.
Figure 2:
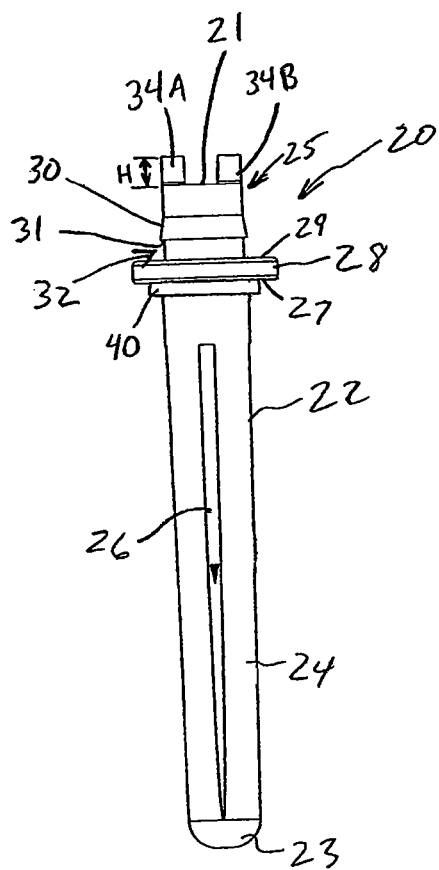
FIG. 2 is a front elevation view of the stem of the prosthesis assembly of FIG. 1.
Figure 3:
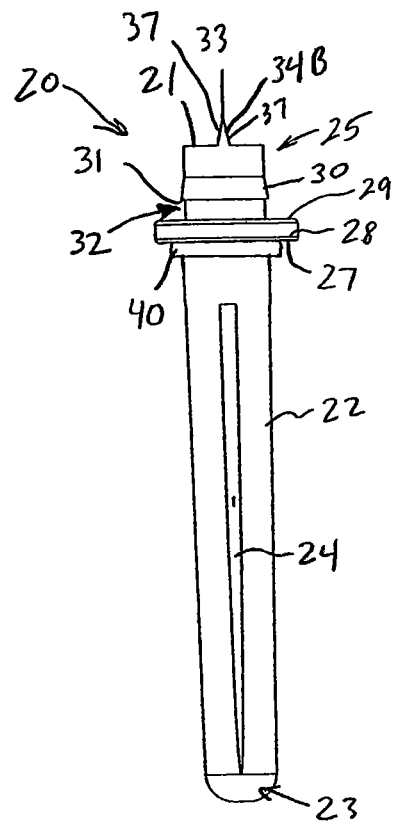
FIG. 3 is a side elevation view of the stem of the prosthesis assembly of FIG. 1.
Figure 4:
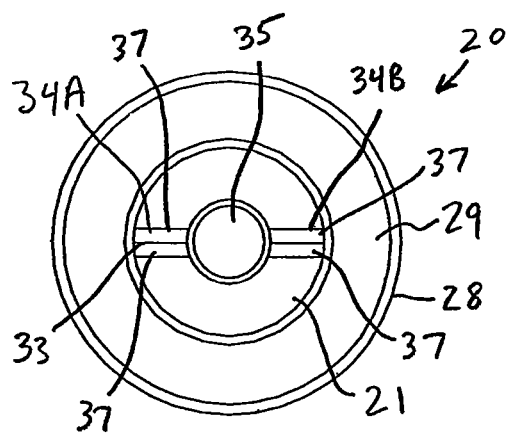
FIG. 4 is a top plan view of the stem of the prosthesis assembly of FIG. 1.

Referring to FIGS. 2-4, the stem 20 has an elongate body 22 extending between a proximal end 23 and a distal end 25. The stem body 22 is manufactured from cobalt chrome, titanium or any other high strength, medical grade material including high temperature and high performance thermoplastic and thermoset polymers. An exemplary material is ASTM F136 Ti6AlV4. The proximal end 23 of the stem 20 is configured for insertion in the intramedullary canal of an ulnar bone. In the present embodiment, the proximal end 23 is tapered such that the stem body 22 narrows toward the proximal end 23 to facilitate insertion within the intermedullary canal. While the stem 20 may be cemented or otherwise retained in the canal, it is preferably retained therein via a friction fit or press fit. The proximal end 23 of the stem 20 is preferably formed with a roughened surface 24 to increase the friction fit and increase the bony ingrowth. An illustrative roughened surface 24 may be provided via a Ti plasma spray coating, however, other methods of providing a roughened surface 24 may also be utilized. Longitudinally extending flutes 26 may be provided along the proximal end 23 of the stem body 22 to prevent rotation of the stem 20 within the intermedullary canal.

A radially extending collar 28 is provided about the stem body 22 proximate to the distal end 25 of the stem 20. The collar 28 has a proximal surface 27 and a distal surface 29. The proximal surface 27 and the distal surface 29 are configured to contact the locking edge of the stem extraction and insertion tool and the proximal collar 40 defines a stop surface to prevent over insertion of the stem 20. The proximal surface 27 also provides a gripping surface that assists in head attachment as described hereinafter.

The distal surface 29 of the collar 28 defines a stop surface for the head 50. A tapered head locking flange 30 is provided about the distal end 25 of the stem body 22 distally of the collar 28. The locking flange 30 defines a proximally facing shoulder 31 spaced a distance from the distal surface 29 of the collar 28. A locking groove 32 is thereby defined between the distal surface 29 of the collar 28 and the shoulder 31 of the locking flange 30. The locking groove 32 is configured to receive and retain a proximal engagement portion 58 of the head 50, as described hereinafter.

One or more locking projections 34A and 34B extend longitundinally from an end surface 21 of the proximal end 25 of the stem 20. In the present embodiment, each locking projection 34A, 34B tapers from the end surface 21 to a pointed edge 33. Each projection 34A, 34B has a width W such that the tapering surfaces thereof define contact surfaces 37 which are configured to engage the head 50 and prevent rotation thereof, as described below. In the present embodiment, two projections 34A and 34B are provided spaced apart by an opening 35 and extending at 180° relative to one another. More or fewer projections may be utilized. For example, three projections spaced apart by 120° or four projections spaced apart by 90° may be utilized. Alternatively, a single projection 34' may be utilized as illustrated with the stem 20' in FIG. 13. The projection 34' extends across the diameter of the end surface 21', having a width equal thereto. With respect to the stem 20" illustrated in FIG. 14, the distal end 25" includes a plurality of projections 34" extending about the circumference of the end surface 21" and configured for engagement with the head 50, as described hereinafter. Other configurations of engagement projections may also be utilized provided they are configured to engage the head 50 and prevent rotation thereof relative to the stem 20.

Figure 5:
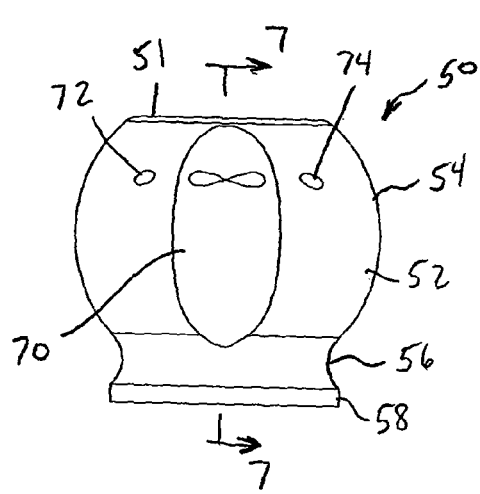
FIG. 5 is a front elevation view of the head of the prosthesis assembly of FIG. 1.
Figure 6:
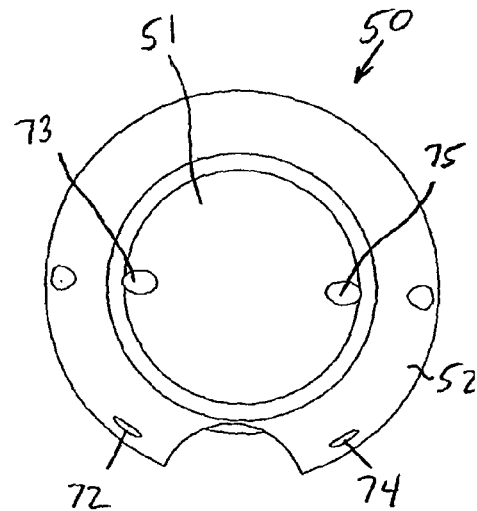
FIG. 6 is a top plan view of the head of the prosthesis assembly of FIG. 1.
Figure 7:
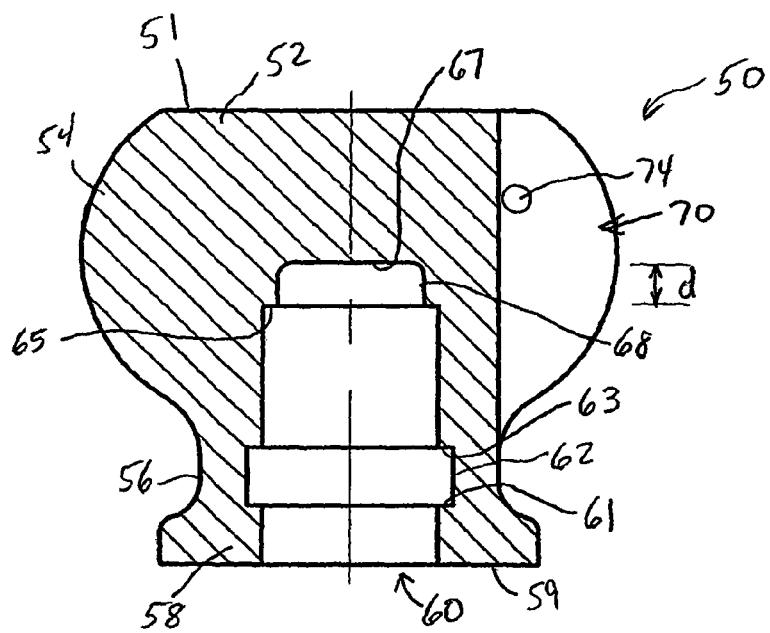
FIG. 7 is a cross-sectional view along the line 7-7 in FIG. 5.

Referring to FIGS. 5-7, an exemplary embodiment of a head 50 in accordance with the present invention will be described. The head 50 has a body 52 terminating in an end surface 51. A spherical portion 54 depends from the end surface 51 and is configured for articulation within the sigmoid notch of the distal radius. The proximal end of the spherical portion 54 extends inward to a neck portion 56 which in turn extends to a proximal engagement portion 58. The head 50 may be manufactured from various medical grade thermoplastic or thermoset polymeric materials or polymeric composites which provide a smooth articulation surface with desired strength and slight deformable elasticity, as described below. A desirable material for the head 50 is ultra high molecular weight polyethylene (UHMWPE) available from Royal DSM N.V. in Greenville, N.C.

As illustrated in FIG. 7, an attachment bore 60 extends through an end surface 59 of the engagement portion 58 and into the body 52 of the head 50. The attachment bore 60 has a generally consistent diameter and is configure to receive the distal end 25 of the stem 20. The diameter of the attachment bore 60 is less than the diameter of the locking flange 30, however, the attachment bore 60 includes an internal attachment groove 62 formed thereabout and configured to receive the locking flange 30. The attachment groove 62 defines an attachment shoulder 61 at the proximal engagement portion 58 and a stop shoulder 63 further therein. The material of the head 50 along with the reduced thickness neck portion 56 of the head 50 allows the engagement portion 58 of the head 50 to flex outward as the locking flange 30 passes through the attachment bore 60 past the engagement portion 58. Once the distal end 25 of the stem 20 is inserted an appropriate amount, the locking flange 30 is received in attachment groove 62 and the engagement portion 58 is received in the locking groove 32 and returns to its original configuration. The proximally facing shoulder 31 of the stem 20 engages the attachment shoulder 61, see FIG. 8, thereby axially locking the head 50 to the stem 20.

Figure 8:
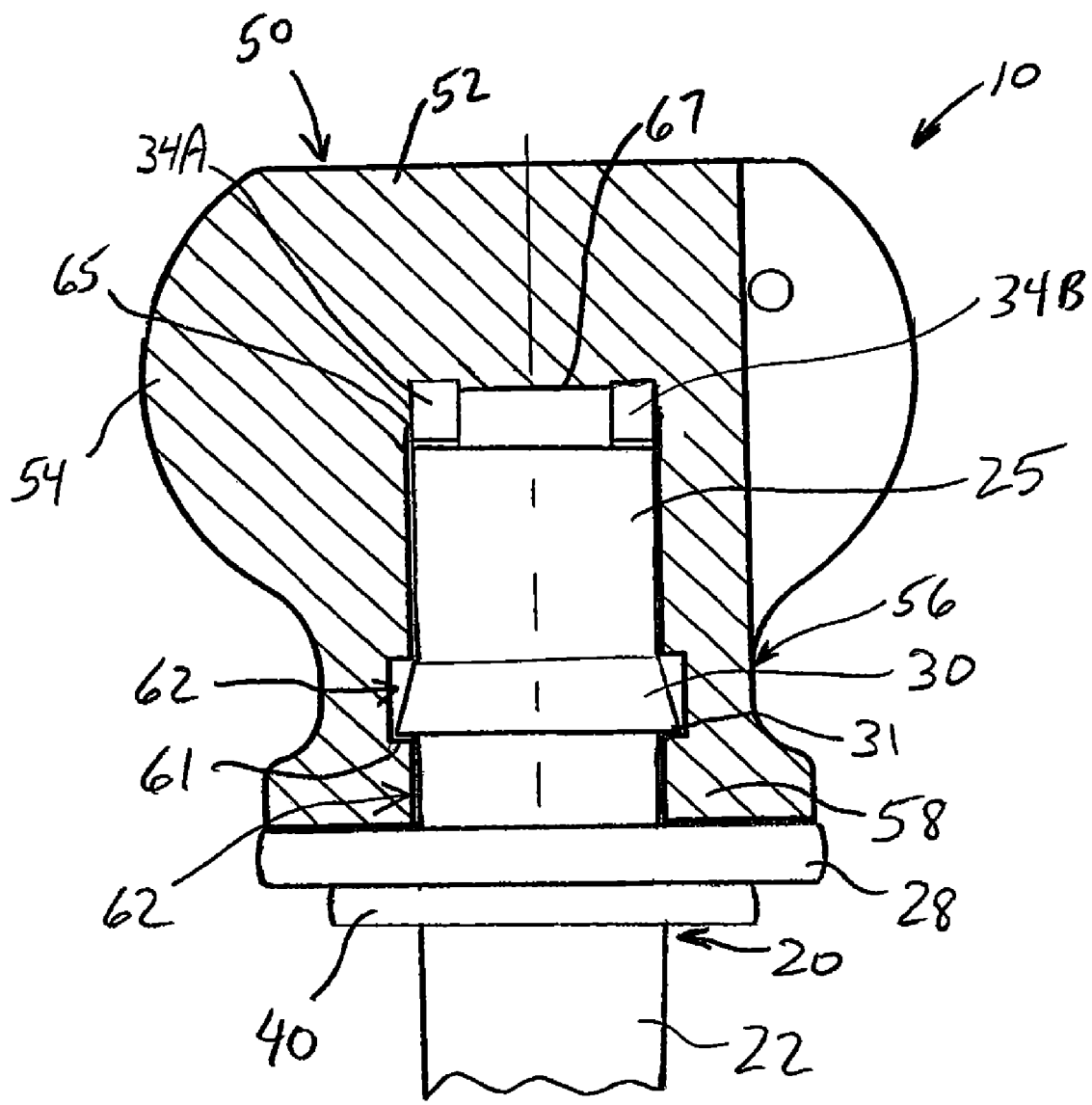
FIG. 8 is a cross-sectional view similar to FIG. 7 showing the head positioned on the stem.

The attachment bore 60 also includes a reduced diameter portion 68 adjacent its internal end wall 67. The reduced diameter portion 68 thereby defines annular end shoulder 65. The end shoulder 65 is configured to be engaged by the engagement projections 34A and 34B as illustrated in FIG. 8. The head 50 material is chosen such that as the engagement projections 34A and 34B engage the end shoulder 65, the projections 34A and 34B penetrate the end shoulder 65 as the end shoulder 65 deforms about the engagement projections 34A and 34B. In the present embodiment, the engagement projections 34A and 34B, preferably have a height H, see FIG. 2, that is greater than the depth d, see FIG. 7, of the reduced diameter portion 68, such that the engagement projections 34A and 34B also engage and penetrate the end wall 67. With the engagement projections 34A and 34B engaged with the end shoulder 65 and the end wall 67, the head 50 is substantially rotationally fixed relative to the stem 20.

Figure 9:
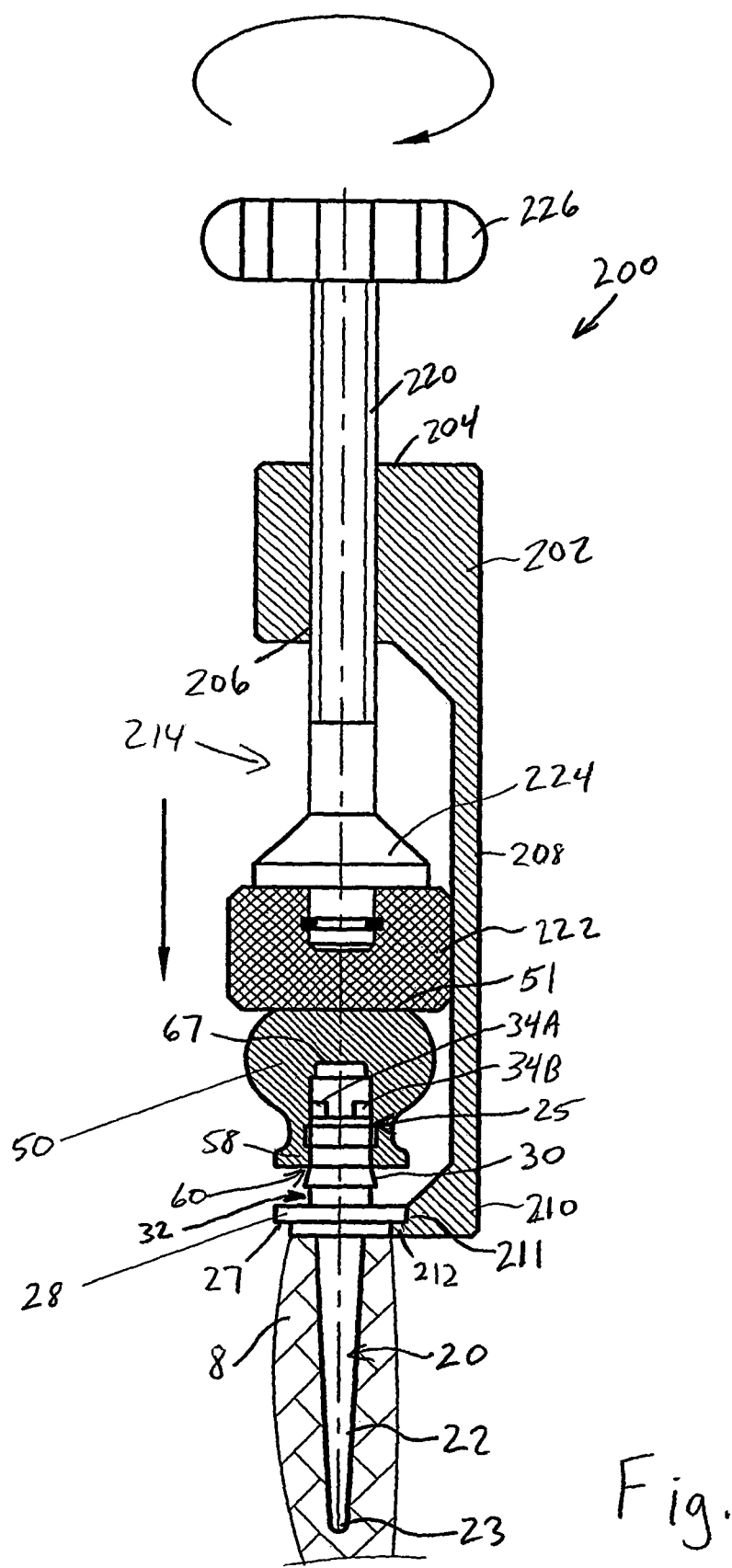
FIG. 9 is a side elevation view, in partial section, illustrating connection of a head to an implanted stem.

Assembly of the head 50 onto the stem 20 and an exemplary assembly tool 200 will be further described with reference to FIG. 9. The stem 20 is implanted with the proximal end 23 fixed in the intramedullary canal of a the distal ulnar bone 8 using known techniques. With the stem 20 so implanted, the collar 28 is accessible external to the distal ulnar bone 8. The assembly tool 200 includes a body 202 with a support portion 204 connected to a foot portion 210 by a bridging portion 208 extending therebetween. The foot portion 210 includes an engagement notch 211 which defines a collar engaging surface 212. The tool body 202 is positioned relative to the stem 20 such that the collar engaging surface 212 engages the proximal surface 27 of the collar 28.

With the tool body 202 so positioned, the distal end 25 of the stem 20 extends into an open area 214 of the tool assembly 200. The head 50 is positioned within the open area 214 and placed on the stem distal end 25 such that the distal end 25 is received in the attachment bore 60 until the locking flange 30 begins to contact the engagement portion 58 of the head 50. A threaded shaft 220 extends through a threaded opening 206 in the support portion 204 and terminates in a transition assembly 224 attached to a pressure block 222. The transition assembly 224 is configured such that it will apply axial motion of the shaft 220 to the pressure block 222 without causing rotation of the pressure block 222. A handle 226 or the like is provided at the opposite end of the shaft 220 and is configured to facilitate rotation of the shaft 220.

To assemble the head 50 to the stem 20, the pressure block 222 is engaged upon the end surface 51 of the head 50. As the handle 226 is rotated, the threaded 220 is caused axially, which in turn causes the pressure block 222 to move axially toward the foot portion 210. Again, the transition assembly 224 provides axial motion to the pressure block 222 without causing rotation to the pressure block 222. As the pressure block 222 is moved axially toward the foot portion 210, it applies an axial force to the head 50 such that the head 50 is forced onto the stem 20, with the engagement portion 58 flexing over the locking flange 30 as described above. The handle 226 is rotated until the head 50 is fully positioned on the stem distal end 25 with the locking flange 30 received in the attachment groove 62, the engagement portion 58 received in the locking groove, and the projections 34A, 34B engaged with the end shoulder 65 and the end wall 67. The operator will feel a tactile sensation as the engagement portion 58 snaps into the locking groove 32, thereby providing confirmation that the head 50 is fully assembled to the stem 20. Additionally, a known axial force will typically be determined for each head 50 and stem 20 arrangement such that the operator knows ahead of time the necessary axial force to achieve proper attachment.

This is contrary to modular head and stem designs utilizing a tapered stem distal end to provide a friction fit. The amount of securing axial force necessary for proper attachment is left completely to the discretion of the operator without any indication when such has been achieved. Additionally, in such systems, the axial force is typically supplied using a mallet or the like with one or more successive blows to the head. This further causes a random application of axial force.

In trials using a stem 20 manufactured from ASTM F136 Ti6AlV4 and a head manufactured from UHMWPE, it was found that an average assembly force of 50 lbs. was necessary to fully assemble the head 50 to the stem 20. Engagement of the proximally facing shoulder 31 of the stem 20 with the attachment shoulder 61 within the head 50 securely maintained the components attached and required an average axial disassembly force of 112 lbs. to disassemble the head 50 from the stem 20. Similarly, engagement of the projections 34A, 34B with the end shoulder 65 and end wall 67 provided a secure rotational connection between the components with an average torsional torque of 4.75 inch-lbs. necessary torsionally separate disassemble the head 50 and stem 20. These disassembly force values represent high values which are unlikely to occur in a patient, thereby providing a desired stability of the prosthesis ulnar head 50.

Referring again to FIGS. 5-7, another feature of the exemplary head 50 will be described. One side of the head 50 includes a suture notch 70 extending axially therealong. One or more suture holes 72, 74 extend from an outside surface of the head 50, through the head body 52 and terminate within the notch 70. Similarly, one or more suture holes 73, 75, may extend from the head end surface 51, through the head body 52, and terminate along the outside surface of the head 50. The suture holes 72-75 provide attachment points for attaching the wrist soft tissue to the prosthetic head 50. While head 50 is shown with four suture holes 72-75, more or fewer holes may be provided. Additionally, the arrangement and location of the suture holes 72-75 is not limited to the configuration shown.

Figure 10A:
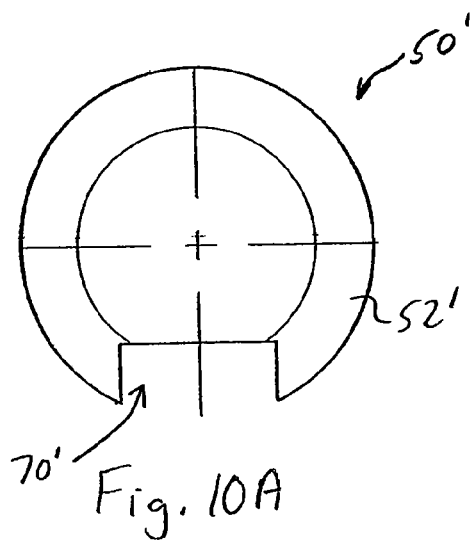
FIGS. 10A and 10B are a top plan view and a cross-sectional view, respectively, of a head in accordance with an alternative embodiment of the present invention.
Figure 10B:
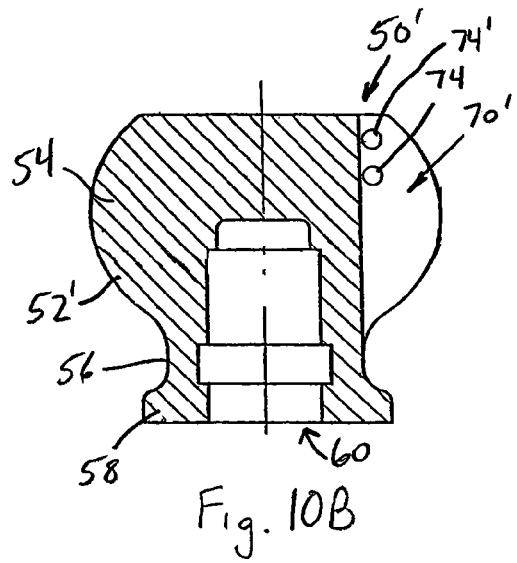

Furthermore, while the notch 70 of the present embodiment has a semicircular shape, the invention is not limited to such. For example, in the head 50' shown in FIGS. 10A and 10B, the suture notch 70' extending along head body 52' has a rectangular configuration. Additionally, two adjacent suture holes 74 and 74' are showing extending through the same surface of the suture notch 70'. In all other respects, the head 50' is the same as described in the previous embodiment.

Figure 11A:
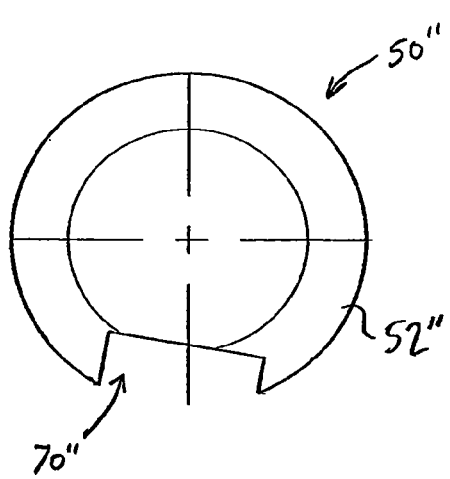
FIGS. 11A and 11B are a top plan view and a cross-sectional view, respectively, of a head in accordance with another alternative embodiment of the present invention.
Figure 11B:
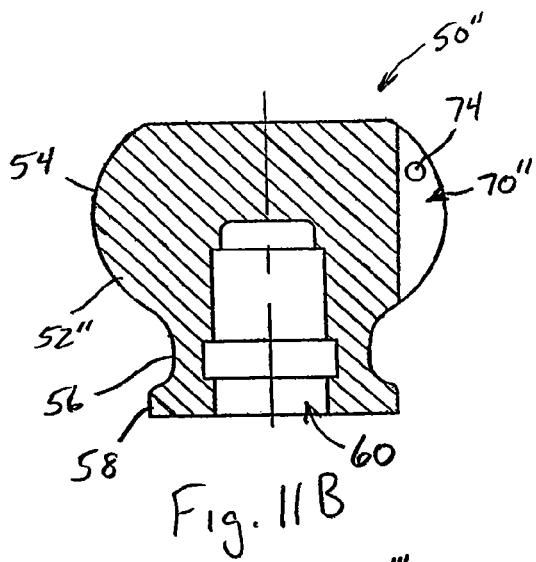

Referring to FIGS. 11A and 11B, the head 50" includes a skewed rectangular suture notch 70" extending along head body 52". That is, the sides of the notch 70" do not extend parallel to a plane extending through the center of the head 50". In all other respects, the head 50' is the same as described in the previous embodiments.

Figure 12A:
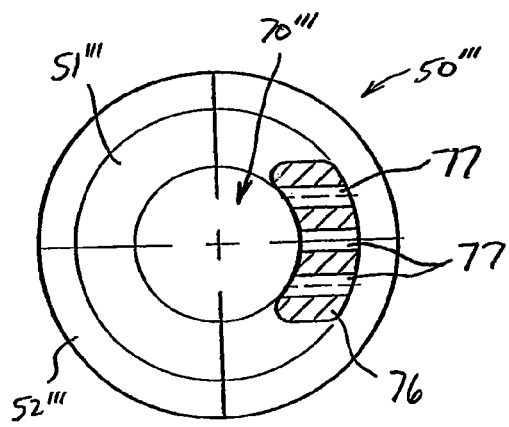
FIGS. 12A and 12B are a top plan view and a cross-sectional view, respectively, of a head in accordance with another alternative embodiment of the present invention.
Figure 12B:
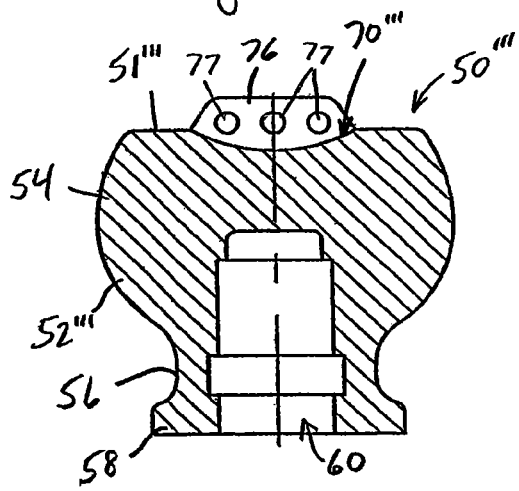

Referring to FIGS. 12A and 12B, the head 50'" does not include an axial notch, but instead includes a suture notch 70'" along the end surface 51'" of the head body 52'". An arcuate suture extension 76 extends axially from the end surface 51'" adjacent to the notch 70'". The suture extension 76 and notch 70"" represent the anatomic process ulna styloid where by stabilizing native soft tissue may be attached with sutures. The suture extension 76 is illustrated with three suture holes 77 extending therethrough. Again, more or fewer holes may be provided. Additionally, while a notch 70''' is provided to allow the height of the suture extension 76 to be minimized, such may not be required. In all other respects, the head 50' is the same as described in the previous embodiments.

Figure 13:
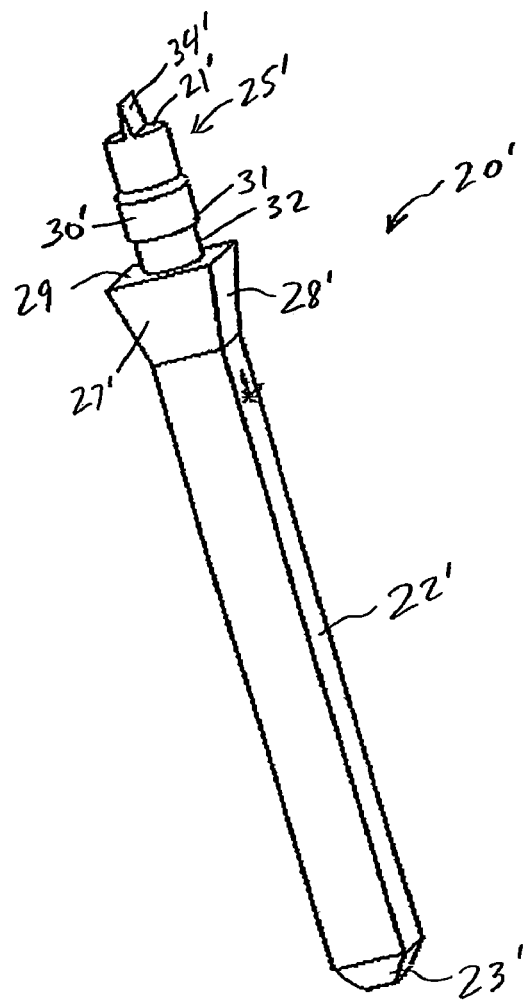
FIG. 13 is an isometric view of a stem in accordance with an alternative embodiment of the present invention.

Referring to FIG. 13, a stem 20' that is another exemplary embodiment of the present invention is shown. Stem 20' is similar to stem 20 and includes a body 22' extending between a proximal end 23' and a distal end 25'. In the present embodiment, the proximal end 23' of the stem body 22' has a rectangular configuration which helps to minimize rotation of the stem 20'. In the present embodiment, the radial collar 28 is replaced with a tapered collar 28' which tapers from the proximal end thereof outwardly toward the distal surface 29. The tapered collar 28' provides four proximal surfaces 27' which do to the taper are configured to be engaged by an assembly tool similar to assembly tool 200 described above. Stem 20' also includes a locking flange 30' which defines a locking shoulder 31 with a locking groove 32 defined between the locking shoulder 31 and the distal surface 29 of tapered collar 28'. As explained above, the distal end 25' of stem 20' includes a single engagement projection 34' extending from the end surface 21'. The engagement projection 34' has a width equal to the diameter of the end surface 21'. In all other respects, the stem 20' is the same as described in the previous embodiments.

Figure 14:
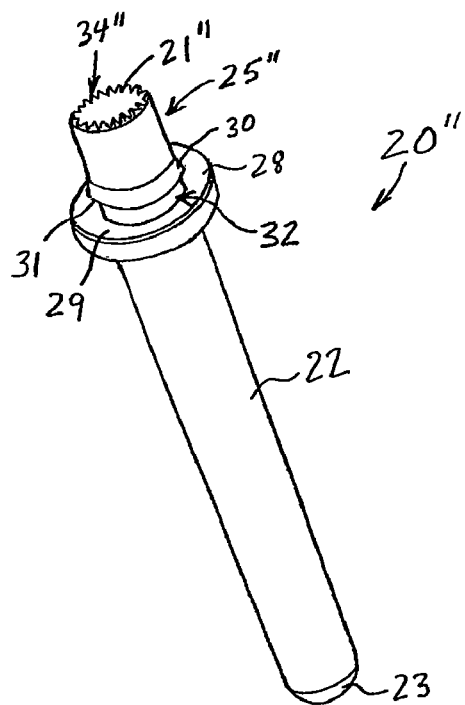
FIG. 14 is an isometric view of a stem in accordance with an alternative embodiment of the present invention.

Referring to FIG. 14, a stem 20'' that is another exemplary embodiment of the present invention is shown. Stem 20'' is similar to stem 20 with the only distinction being the configuration of the engagement projections 34'' at the distal end 25'' of the stem body 22. The distal end 25'' includes a plurality of projections 34'' extending about the circumference of the end surface 21'' to substantially define a serrated end surface 21'''. In the present embodiment, the engagement projections 34'' do not extend beyond the end surface 21'' and therefore will only engage the end shoulder 65 within the head 50. In all other respects, the stem 20'' is the same as described in the previous embodiments.

Figure 15:
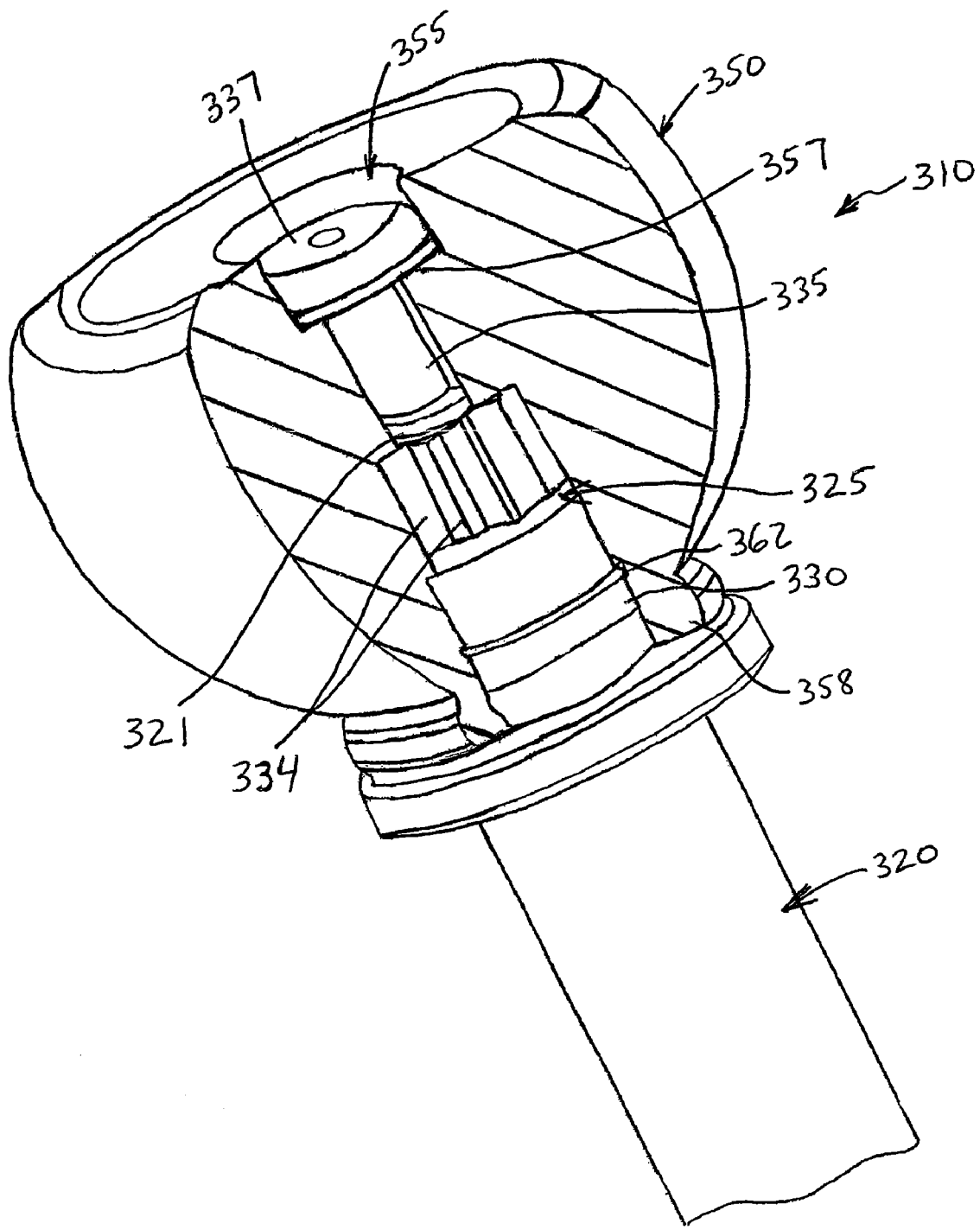
FIG. 15 is an isometric view, in partial section, of a portion of a prosthesis assembly in accordance with another embodiment of the present invention.
Figure 16:
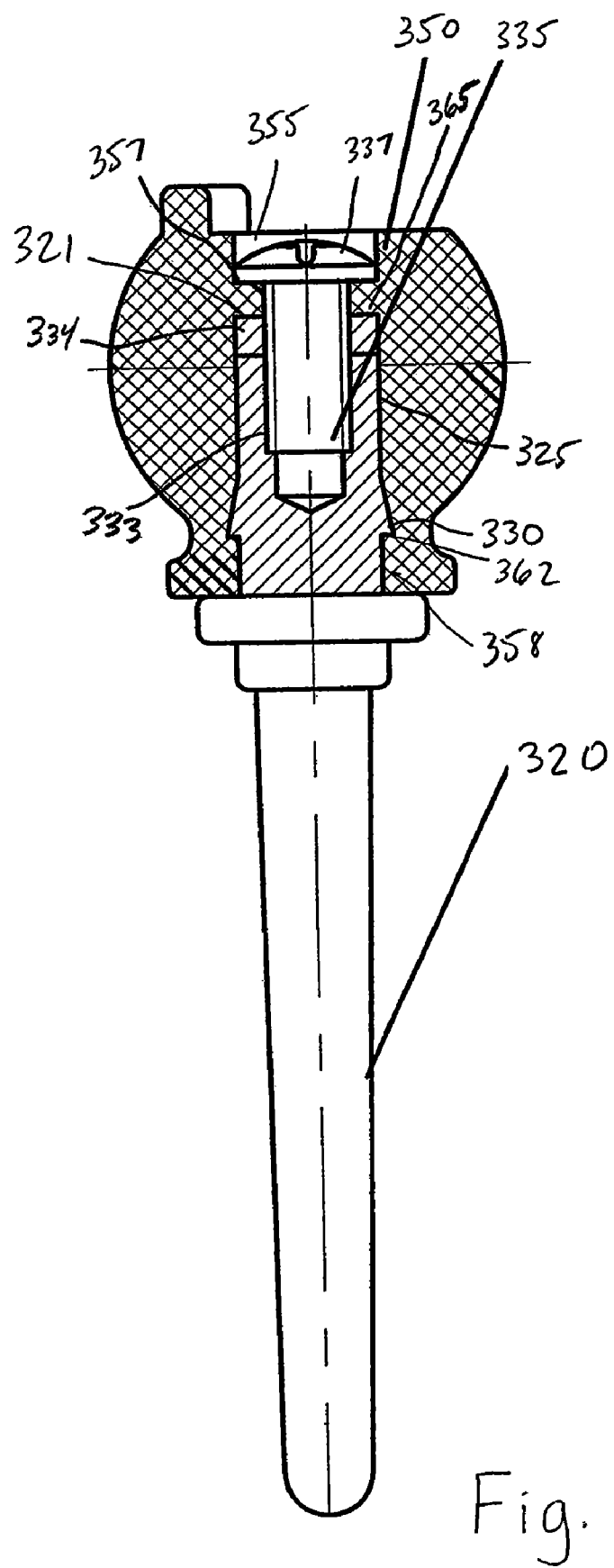
FIG. 16 is a front elevation view, in partial section, of the prosthesis assembly of FIG. 15.

Referring to FIGS. 15 and 16, a prosthesis assembly 310 in accordance with another embodiment of the invention is shown. The prosthesis assembly 310 is similar to the embodiments described above, with only the differences described in detail herein. The prosthesis assembly 310 includes a stem 320 that is mateable with a head 350. The stem 320 is substantially the same as the stem 20'' and includes a plurality of projections 334 extending about the circumference of the end surface 321 to substantially define a serrated end surface 321. In the present embodiment, the distal end 325 of the stem body 322 includes a screw receiving bore 333 extending through the end surface 321. The bore 333 is configured to receive a locking screw 335 passed through a stepped opening 355 in the head 350. The bore 333 may be a threaded bore or an unthreaded bore, in which case the locking screw 335 could be a self-tapping screw.

In use, the prosthesis assembly 310 is similar to the previous embodiments. After the stem 320 is implanted, the head 350 is placed on the stem distal end 325 such that the distal end 325 is received in the attachment bore 360. axial force is applied to the head 350 such that the head 350 is forced onto the stem 320, with the engagement portion 358 flexing over the locking flange 330 and then the locking flange 330 being received in the attachment groove 362, the engagement portion 358 received in the locking groove, and the projections 334 engaged with the end shoulder 365. With the head 350 positioned on the stem 320, the locking screw 335 is positioned through the stepped opening 355 and threadably engaged in the bore 333. The screw head 337 engages a shoulder 357 defined in the stepped opening 355 and further minimizes the chance for inadvertent axial displacement between the head 350 and the stem 320. In other respects, the prosthesis assembly 310 is the same as described in the previous embodiments.

Figure 17:
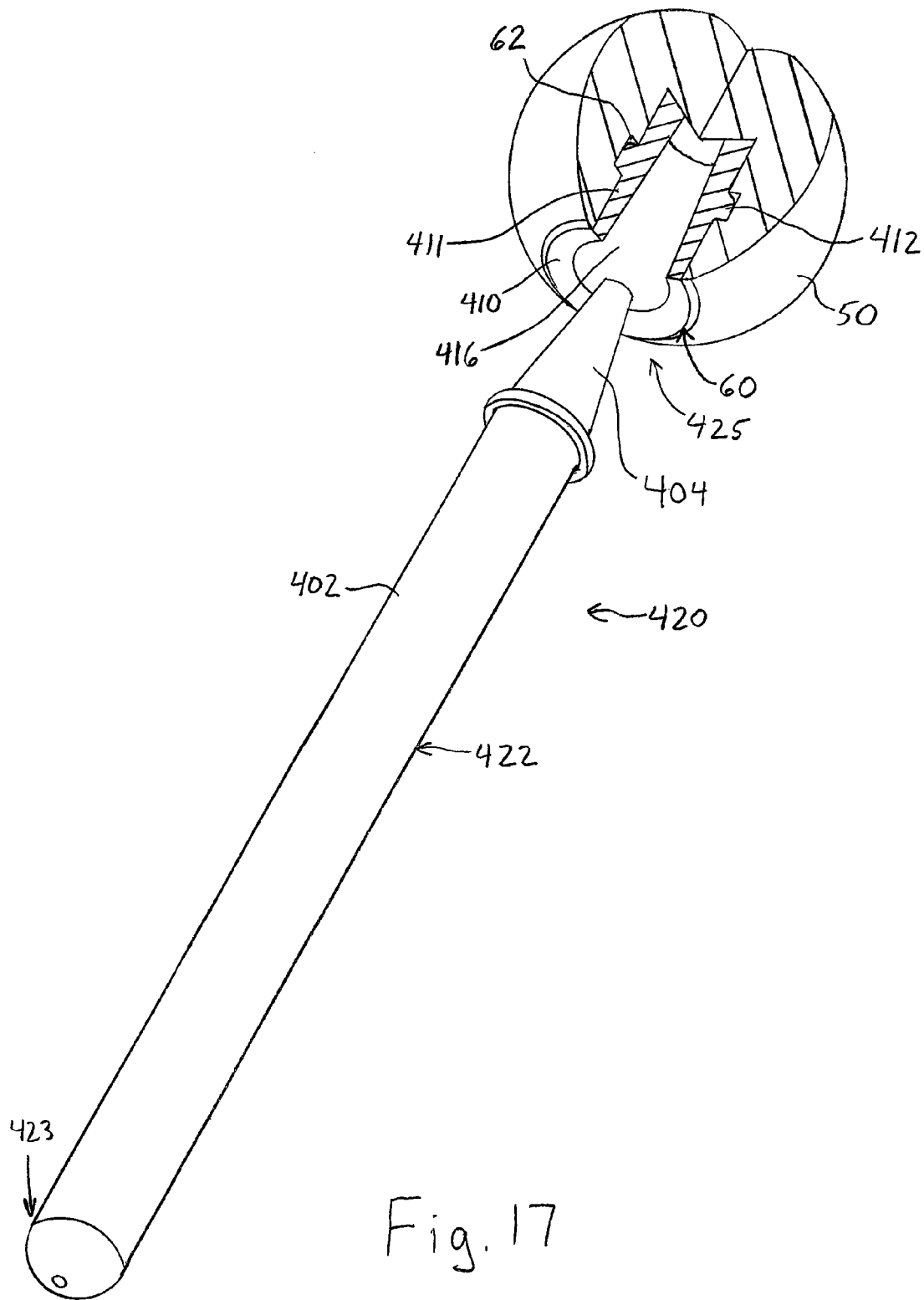
FIG. 17 is a partially exploded isometric view, in partial section, of a prosthesis assembly in accordance with yet another embodiment of the present invention.
Figure 18:
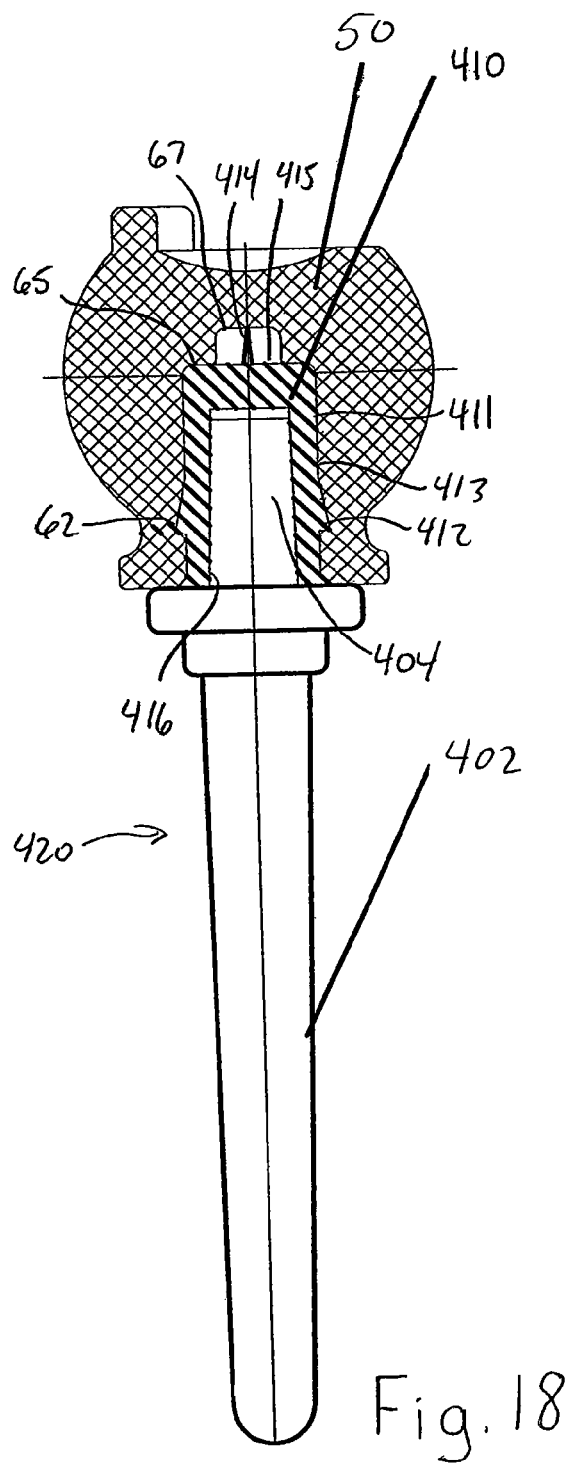
FIG. 18 is a front elevation view, in partial section, of the prosthesis assembly of FIG. 17.
Figure 19:
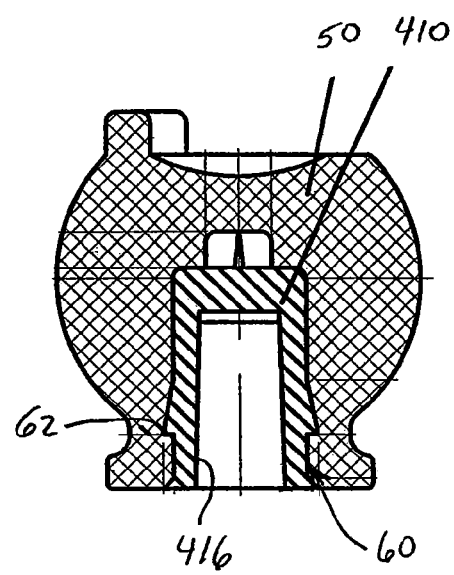
FIG. 19 is a cross-sectional view of the head and insert of the prosthesis assembly of FIG. 17.

Referring to FIGS. 17-19, a stem 420 that is another exemplary embodiment of the present invention is shown. Stem 420 is similar to stem 20 and includes a body 422 extending between a proximal end 423 and a distal end 425, however, the body 422 is a modular component including a primary body portion 402 and an insert portion 410. The insert portion 410 has a generally cylindrical body 411 with a radial projection 412 extending from its side wall 413 and an axial projection 414 extending from the end surface 415. The radial projection 412 serves the function of the locking flange in the previous embodiments and is configured to engage the attachment groove 62 in the head 50. The radial projection 412 can have any of the configurations described herein. The axial projection 414 serves the function of the engagement projections in the previous embodiments and is configured to engage the shoulder 65 and/or end wall 67 in the head 50. The axial projection 414 can have any of the configurations described herein.

Within the cylindrical body 411 is a tapered bore 416 configured to receive a tapered distal end 404 of the primary body portion 402. The tapered distal end 404 and the tapered bore 416 are preferably configured to provide a morse taper fit therebetween such that the primary body portion 402 is axially and rotationally locked relative to the insert portion 410.

The insert portion 410 may be assembled to the primary body portion 402 prior to implantation in which case the assembled modular stem 420 is utilized as described above. Alternatively, the insert portion 410 may be assembled within the attachment bore 60 of the head 50 as shown. As such, the stem primary body portion 402 is implanted and thereafter the tapered end 404 is positioned within the tapered bore 416 and an axial force is applied to the head 50 until a morse taper fit is established between the primary body portion 402 and the insert portion 410. Preferably, the primary body portion 402 and the insert portion 410 are manufactured from the same or different metals while the head 50 is manufactured from a non-metal as described above. This assembly allows a metal-to-metal morse taper fit while allowing the head 50 to be non-metallic. In all other respects, the stem 420 is the same as described in the previous embodiments.

Referring to FIGS. 20-22, a stem 20''' that is another exemplary embodiment of the present invention will be described along with another exemplary head 50'''' which complements the configuration of the stem 20'''. Stem 20''' is similar to stem 20 and includes a body 22''' extending between a proximal end 23 and a distal end 25'''. Stem 20''' again includes a radial collar 28 with a proximal surface 27 and a distal surface 29 and a secondary or proximal collar 40 is provided adjacent to proximal surface 27. The secondary collar 40 has a diameter less than the diameter of collar 28 such that the proximal surface 27 overhangs the secondary collar 40. The secondary collar 40 contacts the end of the distal ulnar bone and acts as a spacer such that it is easier to engage an assembly tool or the like with the proximal surface 27. This is shown in FIG. 9.

The distal end 25''' of the stem 20''' is substantially the same as in the first embodiment, except that the distal end 25''' includes an axially extended portion 38 between the locking flange 30 and the end surface 21. This extended portion 38 can be configured with various lengths such that the stem 20''' may be utilized in revision cases where there is excessive bone loss, with the extended portion 38 making up the length for the removed bone.

To complement the stem 20''', the head 50'''' is formed with an extended bore portion 69 which corresponds to the extended portion 38 of the stem 20'''. The head 50'''' again includes a body 52'''' with a spherical portion 54, a neck portion 56 and an engagement portion 58. Since the collar 28 and the locking flange 30 remain unchanged in the stem 20''', the attachment groove 62 and the engagement portion 58 remain unchanged in head 50'''' and the snap-fit connection is achieved in the same manner as described above. To compensate for the extended bore portion 69, an extended body portion 57 extends between the neck portion 56 and the engagement portion 58. The length of the extended body portion 57 may be varied to compensate for missing bone of the distal ulna during revision procedures to salvage and restore stability to the distal radioulnar joint after failed Darrach resection or hemiresection arthroplasties. In all other respects, the stem 20''' and the head 50'''' are the same as described in the first embodiment.

Referring to FIGS. 23-25, a stem 120 that is another exemplary embodiment of the present invention will be described along with another exemplary head 150 which complements the configuration of the stem 120. Stem 120 is similar to stem 20 and includes a body 122 extending between a proximal end 123 and a distal end 125. Stem 120 again includes a radial collar 128 with a proximal surface 127 and a distal surface 129, however, radial collar 128 has a flattened side 126. That is, side 126 is substantially straight, while the remainder of the collar 128 extends arcuately. The flattened side 126 of stem collar 128 complements the flattened side 168 of the head 150. The flattened sides 126 and 168 are configured to be positioned against a remaining bone surface when only a portion of the distal ulnar bone is removed for a partial replacement. A remaining portion of the distal ulnar bone 8' is shown in phantom relative to the head 150 in FIG. 25.

With reference to FIGS. 24 and 25, the head 150 includes a body 150 with a generally flat end surface 151. A spherical portion 154 depends from the end surface 151 and is configured, with the remaining distal ulnar bone 8', for articulation within the sigmoid notch of the distal radius. The proximal end of the spherical portion 154 extends inward to a neck portion 156 which in turn extends to a proximal engagement portion 158. As indicated in FIG. 24, in the present embodiment, the spherical portion 154, neck portion 156 and engagement portion 158 extend circumferentially approximately 220° before terminating in the flattened side 168. The invention is not limited to such and other configurations may be utilized.

As in the first embodiment, the head 150 includes an attachment bore 160 extending through an end surface 159 of the engagement portion 158 and into the body 152 of the head 150. The attachment bore 160 has an axis BA which is preferably centered within the head 150. Due to the flattened side 168, this may move the axis BA slightly toward the opposite side compared to the head 50. The attachment bore 160 again includes an internal attachment groove 162 formed thereabout and configured to receive the locking flange 130 of the stem 120. The attachment groove 162 defines an attachment shoulder 161 at the proximal engagement portion 158 and a stop shoulder 163 further therein. The attachment bore 160 also includes a reduced diameter portion 168 adjacent its internal end wall 167. The reduced diameter portion 168 thereby defines annular end shoulder 165. The head 150 also includes a suture extension 176 representing the ulna styloid process with suture holes 177, but other suture configurations may also be utilized.

Referring again to FIG. 23, the distal end 125 extending from the distal surface 129 is similar to that of stem 20 and includes a tapered head locking flange 130 distally of the collar 128. The locking flange 130 defines a proximally facing shoulder 131 spaced a distance from the distal surface 129 of the collar 128. A locking groove 132 is thereby defined between the distal surface 129 of the collar 128 and the shoulder 131 of the locking flange 130. The locking groove 132 is configured to receive and retain the proximal engagement portion 158 of the head 150 similar to the embodiments described above. Additionally, at least one locking projection 134 extends longitundinally from the end surface 121 of the proximal end 125 of the stem 120. As in the previous embodiments, the locking projection 134 is configured to engage the head 150 and prevent rotation thereof. Again, other configurations may be utilized.

As illustrated in FIG. 23, the distal end 125 of stem 120 has a central axis LA that is offset from the central axis SA of the stem body 122. This offsetting corresponds to the offsetting of the attachment bore central axis BA, thereby allowing the distal end 125 to be received centrally in the head 150.

In all other respects, the stem 120 and the head 150 are the same as described in the first embodiment.

Figure 26:
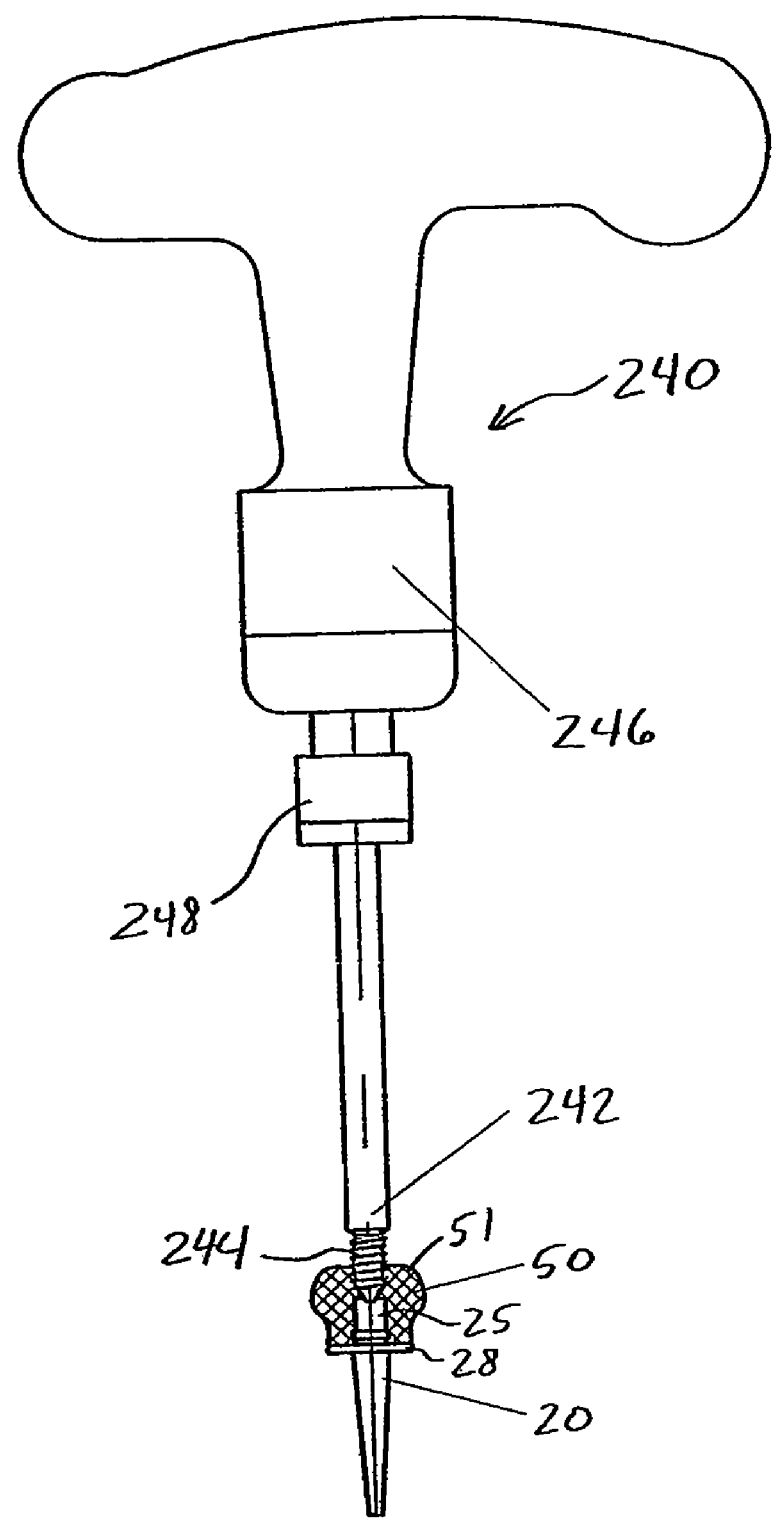
FIG. 26 is a side elevation view illustrating use of a tool to remove a head from an implanted stem.

Referring to FIG. 26, a disassembly tool 220 utilized for disassembling the head 50 from the stem 20 will be described. The disassembly tool 220 includes a shaft 242 with a self-tapping threaded end 244 configured to tap into and engage the head 50 upon rotation of the shaft 242. A ratcheting handle 246 or the like is provided to facilitate rotation of the shaft. Once the shaft 242 has been rotated sufficiently, the threaded end 244 is taps into the head 50 and is threadably engaged therewith. An axial extraction force may then be applied along the shaft 242 to disengage the head 50 from the stem 20. As explained above, in an illustrative embodiment, an axial force of approximately 112 lbs. is necessary to cause axial separation of the head 50 from the stem 20. The axial force may be applied manually to the handle 246 or by a mallet or the like to strike plate 248.

Figure 27:
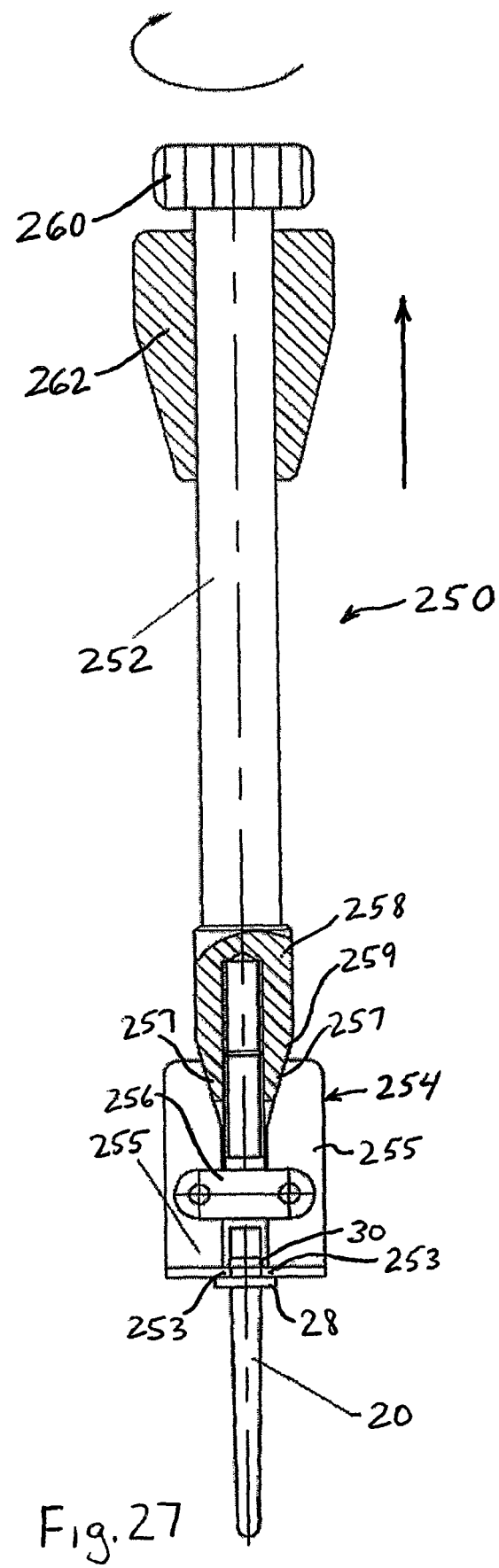
FIG. 27 is a side elevation view illustrating use of a tool to remove an implanted stem.

Referring to FIG. 27, a extraction tool 250 for extracting a stem 20, after the head 50 has been removed, will be described. The extraction tool includes a shaft 252 with a clamp 254 on a proximal end thereof. The clamp 254 includes a pair of opposed clamp members 255 which are pivotally connected about the shaft 252 via pivot support 256 such that each pivots relative to the shaft 252. The proximal end of each clamp member 255 has a foot 253 configured to engage the proximal surface of the stem collar 28. The distal end of each clamp member 255 has an inclined surface 257 that are contacted by an inclined surface 259 of an actuator 258 on the shaft 252. As the shaft 252 is rotated, for example, via handle 262, the actuator 258 is advanced proximally, with the inclined surface 259 engaging the inclined surfaces 257 of the clamp members 255. Upon such engagement of the inclined surfaces 257 and 259, the clamp members 255 are pivoted such that the feet 253 move radially inward and engage the stem collar 28. With the clamp 254 engaged with the collar 28, an axial force may be applied by axially moveable hammer 262 or the like against handle 260.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. An ulnar prosthesis assembly comprising:
a head formed with a curved surface extending between opposed ends, one of the ends having an attachment bore defined therein, the attachment bore generally having a first diameter and including an attachment groove extending about a circumference thereof with a second diameter greater than the first diameter to define at least one attachment shoulder extending about the complete circumference of the bore; and
a stem having a stem body extending between a proximal end configured for implantation in a target bone and a distal end configured to be received in the attachment bore, the distal end having a locking flange extending radially therefrom, the locking flange defining a locking shoulder having a diameter greater than the first diameter such that upon receipt in the attachment bore, the locking shoulder engages the attachment shoulder
wherein the locking flange is tapered outwardly toward the proximal end.

2. An ulnar prosthesis assembly according to claim 1 wherein the stem includes a radial collar with a locking groove defined between the locking shoulder and a distal surface of the radial collar.

3. An ulnar prosthesis assembly according to claim 2 wherein the radial collar includes a tapered proximal surface opposite to the distal surface.

4. An ulnar prosthesis assembly according to claim 1 wherein a reduced diameter neck portion is defined between the curved surface and an engagement portion defined about the attachment bore.

5. An ulnar prosthesis assembly according to claim 1 wherein the head is manufactured from a medical grade thermoplastic or thermoset polymeric material or a polymeric composite material.

6. An ulnar prosthesis assembly according to claim 5 wherein the material is elastically deformable.

7. An ulnar prosthesis assembly according to claim 1 wherein the stem is a modular component including a primary body portion and an insert portion with the insert portion defining the distal portion of the stem.

8. An ulnar prosthesis assembly according to claim 7 wherein the primary body portion and the insert portion are joined via a morse taper fit.

9. An ulnar prosthesis assembly according to claim 1 wherein a threaded screw extends through the head and fixedly engages the stem.

10. An ulnar prosthesis assembly comprising:
a head formed with a curved surface extending between opposed ends, one of the ends having an attachment bore defined therein, the attachment bore generally having a first diameter and including an attachment groove extending about a circumference thereof with a second diameter greater than the first diameter to define at least one attachment shoulder extending about the complete circumference of the bore; and
a stem having a stem body extending between a proximal end configured for implantation in a target bone and a distal end configured to be received in the attachment bore, the distal end having a locking flange extending radially therefrom, the locking flange defining a locking shoulder having a diameter greater than the first diameter such that upon receipt in the attachment bore, the locking shoulder engages the attachment shoulder
wherein the distal end of the stem has an extended portion defined between the locking flange and a distal end surface.

11. An ulnar prosthesis assembly according to claim 10 wherein the attachment bore has an extended portion between the attachment groove and a bore end surface which complements the stem extended portion.

12. An ulnar prosthesis assembly comprising:
a head formed with a curved surface extending between opposed ends, one of the ends having an attachment bore defined therein, the attachment bore generally defining a bore end surface and a bore opening opposite thereto; and
a stem having a stem body extending axially between a proximal end configured for implantation in a target bone and a distal end configured to be received axially into the attachment bore opening, the distal end having a distal end surface with at least one projection extending therefrom and configured such that when the distal end is received in the attachment bore, the at least one projection penetrates the bore end surface such that the head material deforms about the at least one projection and prevents relative rotation between the head and the stem.

13. An ulnar prosthesis assembly according to claim 12 wherein an annular end shoulder is defined along the bore end surface with an end wall within the annular end shoulder.

14. An ulnar prosthesis assembly according to claim 13 wherein the at least one projection penetrates both the annular end shoulder and the end wall.

15. An ulnar prosthesis assembly according to claim 13 wherein the at least one projection penetrates only the annular end shoulder.

16. An ulnar prosthesis assembly according to claim 12 wherein the at least one projection includes two spaced apart projections.

17. An ulnar prosthesis assembly according to claim 16 wherein each of the projections has a width and the two projections are spaced 180° apart width their widths extending in the same plane.

18. An ulnar prosthesis assembly according to claim 12 wherein the at least one projection includes a plurality of projections extending circumferentially about the distal end surface.

19. An ulnar prosthesis assembly according to claim 12 wherein the head is manufactured from a medical grade thermoplastic or thermoset polymeric material or a polymeric composite material.

20. An ulnar prosthesis assembly according to claim 19 wherein the material is elastically deformable.

21. An ulnar prosthesis assembly comprising:
a head with a curved surface extending between opposed ends, one of the ends having an ulnar styloid prominence or process with one or more through holes for reattachment of stabilizing soft tissues, the other end having an attachment bore defined therein and having a bore axis, each of the through holes having a hole axis substantially perpendicular to the bore axis; and
a stem having a stem body extending between a proximal end configured for implantation in a target bone and a distal end configured to be received in the attachment bore.

22. An ulnar prosthesis assembly according to claim 21 wherein a notch is defined in the end adjacent to the styloid prominence or process.

23. An ulnar prosthesis stem comprising:
a stem body extending along a stem axis between a proximal end configured for implantation in a target bone and a distal end adapted to be received in an attachment bore of an ulnar prosthesis head, the distal end having a locking flange extending radially therefrom about the complete circumference thereof, the locking flange having a flange axis generally parallel to the stem axis and defining a locking shoulder about the complete circumference of the stem body in a plane generally perpendicular to the stem axis and facing the proximal end.

24. An ulnar prosthesis stem according to claim 23 wherein the distal end has a distal end surface with at least one projection extending therefrom.

25. An ulnar prosthesis stem according to claim 23 wherein the proximal end of the stem body has a first central axis and the distal end of the stem body has a second central axis that is offset relative to the first central axis.

* * * * *